(12) United States Patent
Sharonov et al.

(10) Patent No.: US 9,157,732 B2
(45) Date of Patent: Oct. 13, 2015

(54) METHODS UTILIZING TRIANGULATION IN METROLOGY SYSTEMS FOR IN-SITU SURGICAL APPLICATIONS

(71) Applicant: Covidien LP, Mansfield, MA (US)

(72) Inventors: Alexey Sharonov, Bethany, CT (US); Candido Dionisio Pinto, Monrovia, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/322,264

(22) Filed: Jul. 2, 2014

(65) Prior Publication Data

US 2014/0313523 A1    Oct. 23, 2014

Related U.S. Application Data

(63) Continuation of application No. 13/448,429, filed on Apr. 17, 2012, now Pat. No. 8,780,362.

(60) Provisional application No. 61/487,750, filed on May 19, 2011.

(51) Int. Cl.
*G01B 11/14* (2006.01)
*A61B 5/107* (2006.01)
*G01B 11/02* (2006.01)

(52) U.S. Cl.
CPC .............. *G01B 11/14* (2013.01); *A61B 5/1076* (2013.01); *G01B 11/02* (2013.01)

(58) Field of Classification Search
CPC ........................................................ G01B 11/14
USPC ........................................................... 356/625
See application file for complete search history.

(56) References Cited

U.S. PATENT DOCUMENTS

| | | | |
|---|---|---|---|
| 2,491,476 A | 12/1949 | Brown |
| 2,819,530 A | 1/1958 | Webber |
| 3,817,635 A | 6/1974 | Kawahara |
| 3,943,361 A | 3/1976 | Miller |
| 4,157,859 A | 6/1979 | Terry |
| 4,281,931 A | 8/1981 | Chikama |

(Continued)

FOREIGN PATENT DOCUMENTS

DE         3629435 A1    3/1987
DE    102010025752 A1    1/2012

(Continued)

OTHER PUBLICATIONS

European Search Report from European Application No. EP 12 16 8466 mailed Mar. 26, 2013.

(Continued)

*Primary Examiner* — Roy M Punnoose

(57) ABSTRACT

A first metrology method includes the steps of projecting a first image and a second image, aligning the first image and the second image to form an aligned image of a known size, and determining a dimension of a target object by comparing the aligned image to the target object. A second metrology method includes the steps of projecting a first image and a second image, aligning the first image and the second image to form an aligned image of a known size by synchronously adjusting a zoom factor for projecting the first image and an angle for projecting the second image, and determining a dimension of a target object by comparing the aligned image to the target object.

10 Claims, 3 Drawing Sheets

(56) References Cited

U.S. PATENT DOCUMENTS

| | | | |
|---|---|---|---|
| 4,570,641 A | 2/1986 | Lieber et al. | |
| 4,660,982 A * | 4/1987 | Okada | A61B 1/00096 356/636 |
| 4,834,070 A | 5/1989 | Saitou | |
| 4,902,123 A | 2/1990 | Yoder, Jr. | |
| 4,958,932 A * | 9/1990 | Kegelman | A61B 5/1076 356/636 |
| 4,980,763 A | 12/1990 | Lia | |
| 4,986,262 A | 1/1991 | Saito | |
| 5,061,995 A | 10/1991 | Lia et al. | |
| 5,070,401 A | 12/1991 | Salvati et al. | |
| 5,090,400 A | 2/1992 | Saito | |
| 5,150,254 A | 9/1992 | Saitou | |
| 5,214,538 A | 5/1993 | Lobb | |
| 5,285,785 A | 2/1994 | Meyer | |
| 5,558,666 A | 9/1996 | Dewey et al. | |
| 5,573,492 A | 11/1996 | Dianna et al. | |
| 5,669,871 A * | 9/1997 | Sakiyama | A61B 5/1076 348/135 |
| 5,704,897 A | 1/1998 | Truppe | |
| 5,808,813 A | 9/1998 | Lucey et al. | |
| 5,815,274 A | 9/1998 | Dlugos | |
| 6,009,189 A | 12/1999 | Schaack | |
| 6,070,583 A | 6/2000 | Perelman et al. | |
| 6,096,049 A | 8/2000 | McNeirney et al. | |
| 6,118,535 A | 9/2000 | Goldberg et al. | |
| 6,121,999 A | 9/2000 | Schaack | |
| 6,151,407 A | 11/2000 | Conlon et al. | |
| 6,246,898 B1 | 6/2001 | Vesely et al. | |
| 6,360,012 B1 | 3/2002 | Kreuzer | |
| 6,451,010 B1 | 9/2002 | Angeley | |
| 6,459,760 B1 * | 10/2002 | D'Ambrosio | G01N 23/04 356/625 |
| 6,476,979 B1 | 11/2002 | Schaack | |
| 6,482,148 B1 | 11/2002 | Luke | |
| 6,508,761 B1 | 1/2003 | Ramsbottom et al. | |
| 6,542,763 B1 | 4/2003 | Yamashita et al. | |
| 6,611,698 B1 | 8/2003 | Yamashita et al. | |
| 6,614,036 B1 * | 9/2003 | Reinstein | A61N 5/1049 250/492.3 |
| 6,697,664 B2 | 2/2004 | Kienzle, III et al. | |
| 6,741,338 B2 | 5/2004 | McArthur et al. | |
| 6,977,732 B2 * | 12/2005 | Chen | G01B 11/25 356/603 |
| 7,389,131 B2 | 6/2008 | Kanayama | |
| 7,405,388 B2 * | 7/2008 | Reilley | B23Q 17/2233 250/221 |
| 7,486,805 B2 | 2/2009 | Krattiger | |
| 7,556,599 B2 | 7/2009 | Rovegno | |
| 7,720,532 B2 | 5/2010 | Hashimshony et al. | |
| 7,796,791 B2 | 9/2010 | Tsougarakis et al. | |
| 7,812,968 B2 | 10/2010 | Bendall et al. | |
| 7,862,555 B2 | 1/2011 | Chan et al. | |
| 8,780,362 B2 | 7/2014 | Sharonov et al. | |
| 2003/0013973 A1 | 1/2003 | Georgakoudi et al. | |
| 2003/0191368 A1 | 10/2003 | Wang et al. | |
| 2003/0191397 A1 | 10/2003 | Webb | |
| 2004/0171986 A1 | 9/2004 | Tremaglio et al. | |
| 2004/0176683 A1 | 9/2004 | Whitin et al. | |
| 2004/0223118 A1 * | 11/2004 | Jean | A61B 3/107 351/200 |
| 2005/0020926 A1 | 1/2005 | Wiklof et al. | |
| 2005/0085717 A1 | 4/2005 | Shahidi | |
| 2005/0090749 A1 | 4/2005 | Rubbert | |
| 2005/0124988 A1 | 6/2005 | Terrill-Grisoni et al. | |
| 2005/0180160 A1 | 8/2005 | Nelson | |
| 2005/0237423 A1 | 10/2005 | Nilson et al. | |
| 2005/0261571 A1 | 11/2005 | Willis et al. | |
| 2006/0092418 A1 | 5/2006 | Xu et al. | |
| 2006/0253107 A1 | 11/2006 | Hashimshony et al. | |
| 2008/0024793 A1 | 1/2008 | Gladnick | |
| 2008/0027276 A1 | 1/2008 | Rovegno | |
| 2008/0039742 A1 | 2/2008 | Hashimshony et al. | |
| 2008/0068197 A1 | 3/2008 | Neubauer et al. | |
| 2008/0146915 A1 | 6/2008 | McMorrow | |
| 2008/0200808 A1 | 8/2008 | Leidel et al. | |
| 2008/0218588 A1 | 9/2008 | Stetten | |
| 2008/0221446 A1 | 9/2008 | Washburn et al. | |
| 2008/0319286 A1 | 12/2008 | Ridder et al. | |
| 2009/0002485 A1 | 1/2009 | Fujiwara | |
| 2009/0054767 A1 | 2/2009 | Telischak et al. | |
| 2009/0105564 A1 | 4/2009 | Tokita | |
| 2009/0252290 A1 | 10/2009 | Plut et al. | |
| 2009/0259114 A1 | 10/2009 | Johnson et al. | |
| 2009/0270682 A1 | 10/2009 | Visser | |
| 2009/0270698 A1 | 10/2009 | Shioi et al. | |
| 2010/0022858 A1 | 1/2010 | Gono | |
| 2010/0046004 A1 | 2/2010 | Lee et al. | |
| 2010/0201796 A1 | 8/2010 | Chan | |
| 2011/0019064 A1 | 1/2011 | Stallinga | |
| 2011/0054308 A1 | 3/2011 | Cohen et al. | |
| 2011/0279670 A1 | 11/2011 | Park et al. | |
| 2012/0101370 A1 | 4/2012 | Razzaque et al. | |

FOREIGN PATENT DOCUMENTS

| | | |
|---|---|---|
| EP | 0403399 A2 | 12/1990 |
| EP | 1480067 A1 | 11/2004 |
| EP | 2106748 A1 | 10/2009 |
| JP | 2011185767 A | 9/2011 |
| WO | 0008415 A1 | 2/2000 |
| WO | 2005013814 A1 | 2/2005 |

OTHER PUBLICATIONS

European Search Report from EP 12190094.8 dated Mar. 4, 2013 (6 pgs.).

European Search Report from EP 13156689.5 dated Apr. 26, 2013 (7 pgs.).

European Search Report dated Nov. 28, 2013 in European Appln. No. 13 17 7731.

European Search Report for EP Application No. 13156676.2-1553 dated Jul. 2, 2013. (7 pages).

European Search Report for EP Application No. 12190097.1 dated Sep. 13, 2013. (6 pgs.).

European Search Report for EP Application No. 13172563.2 dated Oct. 1, 2013. (8 pgs.).

* cited by examiner

US 9,157,732 B2

METHODS UTILIZING TRIANGULATION IN METROLOGY SYSTEMS FOR IN-SITU SURGICAL APPLICATIONS

This application is a continuation of U.S. patent application Ser. No. 13/448,429, filed Apr. 17, 2012, which claims the benefit of and priority to U.S. Provisional Patent Application No. 61/487,750, filed May 19, 2011, the entire disclosure of which is incorporated by reference herein.

BACKGROUND

1. Technical Field

The present disclosure relates to a method for measuring a dimension of a target site. More particularly, the present disclosure relates to a method of triangulation for creating an image of a predetermined size for use in measuring a dimension of a target site.

2. Background of the Related Art

Minimally invasive surgery, e.g., laparoscopic, endoscopic, and thoroscopic surgery, has many advantages over traditional open surgeries. In particular, minimally invasive surgery eliminates the need for a large incision, thereby reducing discomfort, recovery time, and many of the deleterious side effects associated with traditional open surgery.

The minimally invasive surgeries are performed through small openings in a patient's skin. These openings may be incisions in the skin or may be naturally occurring body orifices (e.g., mouth, anus, or vagina). In general, insufflation gas is used to enlarge the area surrounding the target surgical site to create a larger, more accessible work area.

During minimally invasive procedures, it is often difficult for a surgeon to determine sizes of various organs, tissues, and other structures in a surgical site. Various in-situ surgical metrology methods exist for measurement in a surgical site. Such methods require many moving parts and projection images that change size and/or focus quickly as projectors move in or out of a surface of projection. A continuing need exists for in-situ surgical metrology methods that operate with a stable focus and no moving parts.

SUMMARY

A first metrology method includes the steps of projecting a first image and a second image, aligning the first image and the second image to form an aligned image of a known size by moving an instrument towards and away from a target object, and determining a dimension of a target object by comparing the aligned image to the target object. The aligned image may include aligned circles. The aligned image may include a single point aligned with a center point of a circle. The projecting of at least one of the first image and second image may be achieved by a point source projector. A single beam may be split to project the first image and the second image.

A second metrology method includes the steps of projecting a first image and a second image, aligning the first image and the second image to form an aligned image of a known size by synchronously adjusting a zoom factor for projecting the first image and an angle for projecting the second image, and determining a dimension of a target object by comparing the aligned image to the target object. The aligned image may include aligned circles. The aligned image may include a single point aligned with a center point of a circle. The projecting of at least one of the first image and second image may be achieved by a point source projector. A single beam may be split to project the first image and the second image.

In other embodiments the metrology system may be a standalone device, while projected pattern is observed through a separate endoscope.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
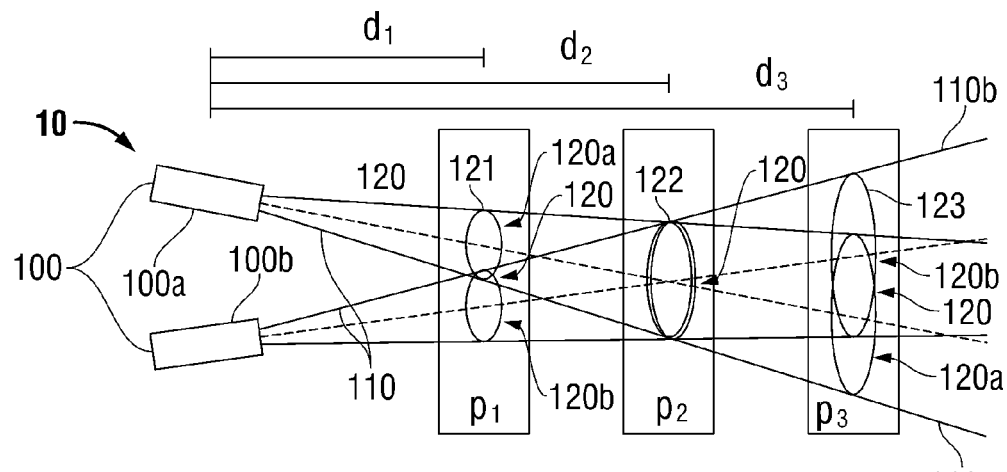
FIG. 1 is a side, schematic view of a metrology system according to the principles of the present disclosure.

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus which is closer to the user and the term "distal" refers to the end of the apparatus which is farther away from the user. The term "clinician" refers to any medical professional (i.e., doctor, surgeon, nurse, or the like) performing a medical procedure involving the use of embodiments described herein.

As seen in FIG. 1, a metrology system 10 according to an embodiment of the present disclosure is illustrated. Metrology system 10 utilizes projectors 100 for projecting light beams 110 at intersecting angles. Projectors 100 include a projector 100a and a projector 100b. Some embodiments may utilize more than two projectors 100. Other embodiments may only have one projector 100, as will be described in greater detail hereinbelow. In metrology system 10, projector 100a and projector 100b are substantially identical and project substantially identical light beams 110a, 110b, respectively.

Light beams 110 form an image 120 including an image 120a from light beam 110a and an image 120b from light beam 110b. Images 120a, 120b substantially align to form a substantially aligned image 122 having a predetermined size on an image plane $p_2$ at a distance $d_2$ from point sources 102 (FIG. 2) of projectors 100. Image plane $p_2$ is the only image plane on which images 120a, 120b align. On an image plane $p_1$ at a distance $d_1$ less than distance $d_2$ from point sources 102 of projectors 100, an unaligned image 121 is formed. Likewise, on an image plane $p_3$ at a distance $d_3$ greater than distance $d_2$ from point sources 102 of projectors 100, an unaligned image 123 is formed. Distance $d_2$ may be calculated geometrically using a distance between point sources 102 and angles of projectors 100. Distance $d_2$ may also be determined experimentally. Similarly, the predetermined size of aligned image 122 may be determined geometrically or experimentally.

Images 120a, 120b may be any shapes appropriate for determining an alignment of thereof. For example, images 120a, 120b may be circles that concentrically overlap on image plane $p_2$. Images 120a, 120b have uniformly spaced markings. In other embodiments, an endoscope or other device may provide uniformly spaced markings. When image 122 is formed, the uniformly spaced markings have a predetermined distance therebetween to assist in determining a measurement of a dimension on image plane $p_2$. The predetermined distance of the uniformly spaced markings may be determined geometrically or experimentally. Although images 120a, 120b are substantially identical in metrology system 10, other embodiments may have differing shapes of images 120a, 120b.

Figure 2:
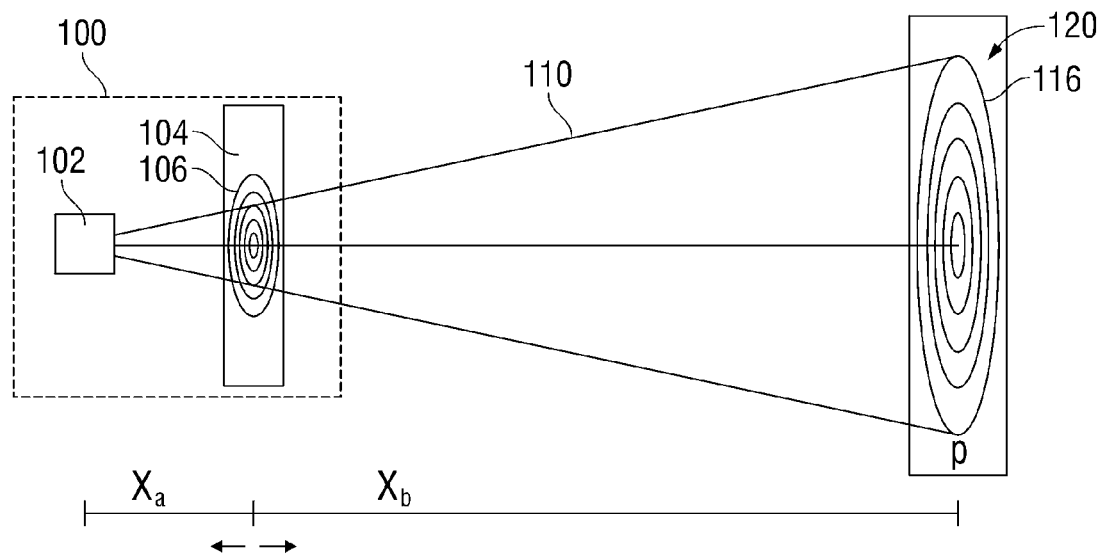
FIG. 2 is a side, schematic view of a projector of the metrology system of FIG. 1.

As seen in FIG. 2, a projector 100 includes a point source 102 and a mask 104. Point source 102 emits a light beam 110. Various embodiments of point source 102 include a laser diode, a light-emitting diode, and a lens for shaping a beam of light. Mask 104 is positioned between point source 102 and the target site. Mask 104 has a pattern 106 disposed thereon in a shape of a desired image 120, such as a series of concentric, uniformly spaced circles. Light beam 110 may be collimated for increased sharpness of image 120. Light beam 110 is partially blocked upon incidence with mask 104. A portion of light beam 110 that passes through mask 104 forms a magnified pattern 116 as a portion of image 120.

A magnification factor of pattern 106 to pattern 116 is calculated according a formula: $M=1+x_b/x_a$, where M is the magnification factor, $x_a$ is a distance between point source 102 and mask 104, and $x_b$ is a distance between mask 104 and the target site. Accordingly, image 120 may be enlarged when $x_b$ is increased or $x_a$ is decreased. Image 120 may shrink upon an increase of $x_a$ or a decrease of $x_b$. Mask 104 may be translated with respect to the target site to increase or decrease $x_a$ and $x_b$. Metrology system 10 may be translated to increase or decrease $x_b$. Point source 102 is sufficiently small for edges of image 120 to remain substantially sharp as a size of image 120 changes.

Figure 3:
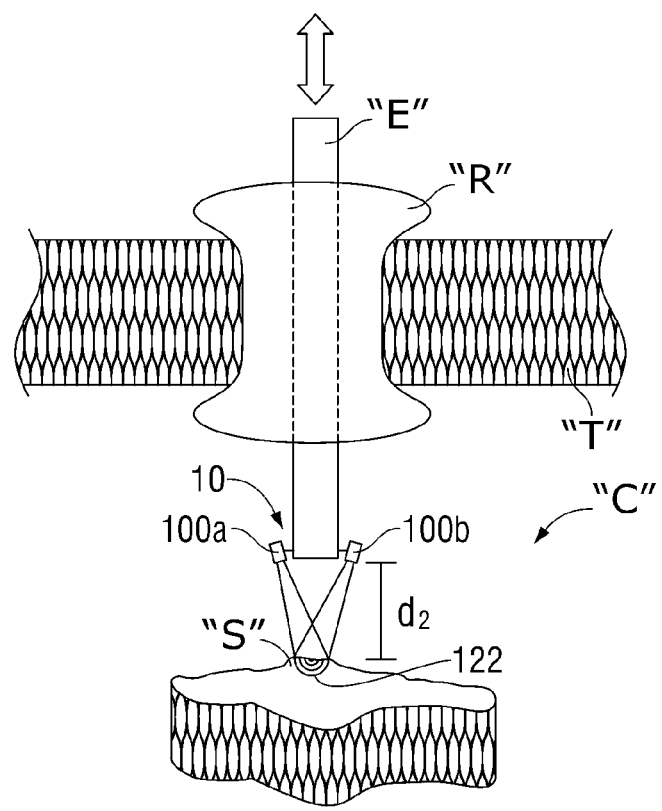
FIG. 3 is a side, perspective view of a method of use of the metrology system of FIG. 1.

A method of use of metrology system 10 will now be described. As seen in FIG. 3, metrology system 10 may be attached to a distal end of an endoscope "E". Endoscope "E" is inserted into a body cavity "C" through an opening in a tissue "T". Endoscope "E" may be inserted through a seal anchor "R" positioned in the opening in tissue "T". Projectors 100 project image 120 onto a target site "S" within cavity "C". A clinician may observe image 120 through endoscope "E". If images 120a, 120b are not aligned, endoscope "E" is translated distally or proximally until point sources 102 of projectors 100 are at distance $d_2$ from target site "S". Once aligned image 122 is formed on target site "S", the predetermined size of aligned image 122 and the predetermined distance of the uniformly spaced markings thereon may be used to measure a dimension of target site "S". A dimension of target site "S" is measured by visually inspecting and counting a number of uniformly spaced markings appearing along the dimension of target site "S". The number of uniformly spaced markings is multiplied by the predetermined distance therebetween to calculate the measure of the dimension of target site "S".

Figure 4:
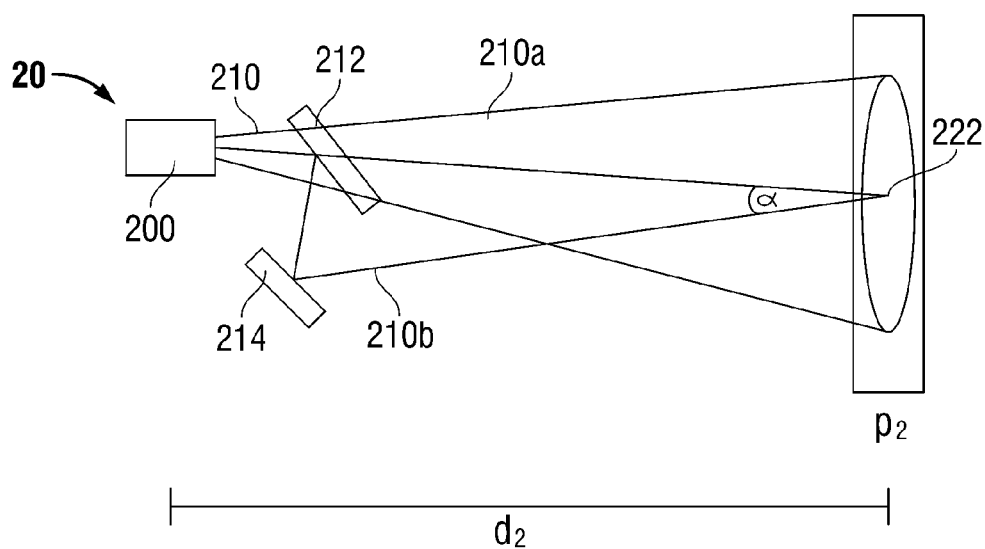
FIG. 4 is a side, schematic view of a metrology system according to another embodiment of the present disclosure.

Turning to FIG. 4, a metrology system in accordance with an alternate embodiment of the present disclosure is generally designated as 20. Metrology system 20 is similar to metrology system 10 and thus will only be discussed as necessary to identify the differences in construction and operation thereof.

Metrology system 20 has a projector 200, a splitter 212, and a reflector 214. Projector 200 is substantially identical to projector 100 (FIG. 2) and projects a light beam 210. Splitter 212 splits light beam 210 into light beams 210a, 210b. Embodiments of splitter 212 include prisms and mirrors. Light beam 210a passes through splitter 212. Light beam 210b is reflected by splitter 212 onto reflector 214. Reflector 214 reflects light beam 210b at an angle $\alpha$ for intersection with light beam 210a.

Light beams 210 form a substantially aligned image 222 on an image plane $p_2$ at a distance $d_2$ from a point source of projector 200. Image plane $p_2$ is the only image plane on which a substantially aligned image is formed. Light beams 210 project a pattern having uniformly spaced markings onto image plane $p_2$. Distance $d_2$, a distance of the uniformly spaced markings, and a size of aligned image 222 may be determined geometrically or experimentally.

Light beams 210 produce images of any shapes appropriate for determining an alignment of thereof. In some embodiments, a total overlap of certain elements of the images of light beams 210 may not occur due to light beam 210a travelling a shorter total distance than light beam 210b to reach image plane $p_2$. In such embodiments, an alignment of a point or a line may be an ideal indicator of alignment. For example, light beam 210a may project a circle with a center point, and light beam 210b may project a single point for aligning with the center point of the image projected by light beam 210a.

A method of use of metrology system 20 is substantially identical to the method of use of metrology system 10 described hereinabove.

Figure 5:
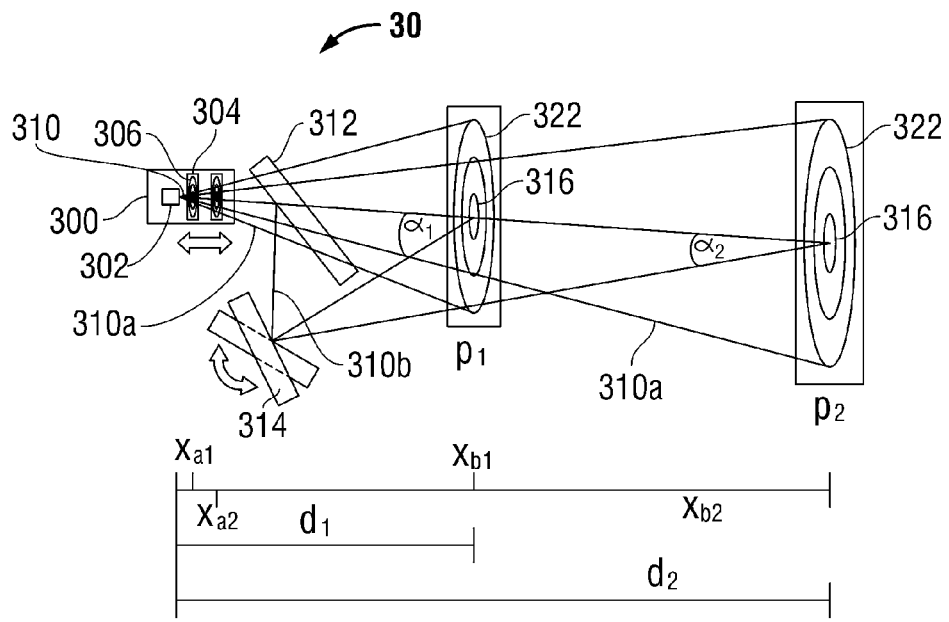
FIG. 5 is a side, schematic view of a metrology system according to another embodiment of the present disclosure.

Turning to FIG. 5, a metrology system in accordance with an alternate embodiment of the present disclosure is generally designated as 30. Metrology system 30 is similar to metrology system 20 and thus will only be discussed as necessary to identify the differences in construction and operation thereof.

Figure 6:
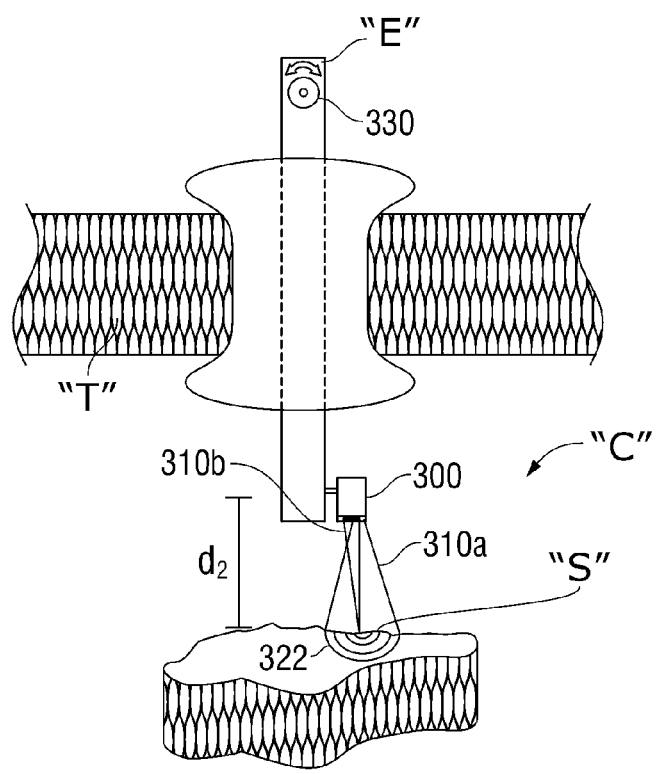
FIG. 6 is a side, perspective view of a method of use of the metrology system of FIG. 5.

Metrology system 30 includes a projector 300, a splitter 312, a reflector 314, and an actuator 330 (FIG. 6). Projector 300 includes a point source 302 and a mask 304. Mask 304 is a distance $x_{an}$ away from point source 302 and distances $x_{bn}$ away from image planes $p_n$. Point source 302 emits a light beam 310 that passes through a pattern 306 on mask 304. Splitter 312 splits light beam 310 into light beams 310a, 310b. Light beam 310a passes through splitter 312 and forms a first image on an image plane $p_n$. Light beam 310b is reflected by splitter 312 onto reflector 314. Reflector 314 is rotatable to reflect light beam 310b at any of angles $\alpha_n$ onto image planes $p_n$ to form a second image. The first image and the second image form a substantially aligned image 322 on an image plane $p_n$ having a distance $d_n$ from point source 302 when reflector 314 reflects light beam 310b at a particular angle $\alpha_n$. For each image plane $p_n$, only angle $\alpha_n$ provides for a projection of substantially aligned image 322. Substantially aligned image 322 has a magnified pattern 316 thereon. Magnified pattern 316 is a magnification of pattern 306 and includes uniformly spaced markings thereon having a predetermined distance on image plane $p_n$.

Actuator 330 is operably coupled to mask 304 and reflector 314. A manipulation of actuator 330 rotates reflector 314, thus changing an angle $\alpha_n$ and an image plane $p_n$ on which aligned image 322 is formed. Actuator 330 translates mask 304 a distance to maintain a predetermined size of image 322. The translation of mask 304 and the rotation of reflector 314 are synchronous upon a manipulation of actuator 330. A relationship between the translation of mask 304 and the rotation of reflector 314 is described according to the following formulas:

$$d_2/d_1 = \tan(\alpha_1)/\tan(\alpha_2) = M_1/M_2$$

$$M = 1 + x_b/x_a$$

$$d = x_a + x_b$$

In the formulas above, the values of $d_1$, $\alpha_1$, and $M_1$ respectively represent an initial distance $d_n$, angle $\alpha_n$, and magnification $M_n$ of system 30. The values of $d_2$, $\alpha_2$, and $M_2$ respectively represent a resulting distance $d_n$, angle $\alpha_n$, and magnification $M_n$ of system 30 after actuator 330 is manipulated.

A method of use of metrology system 30 is similar to the method of use of metrology system 10 described hereinabove. As seen in FIG. 6, metrology system 30 is attached to a distal end of an endoscope "E". Endoscope "E" is inserted into a body cavity "C" through an opening in a tissue "T". Projector 300 projects light beams 310a, 310b onto a target site "S" within cavity "C". A clinician may observe an image formed by light beams 310a, 310b through endoscope "E". If substantially aligned image 322, is not formed on target site "S", actuator 330 is rotated until substantially aligned image 322 is formed on target site "S". The predetermined size of substantially aligned image 322 and the uniformly spaced markings of magnified pattern 316 may then be used to measure a dimension of target site "S".

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figs. are presented only to demonstrate certain examples of the disclosure. Other elements, steps, methods and techniques that are insubstantially different from those described above and/or in the appended claims are also intended to be within the scope of the disclosure.

What is claimed is:

1. A metrology method comprising:
   projecting a first image and a second image on an image plane;
   aligning the first image and the second image on a target site different from the image plane; and
   measuring a dimension of the target site by counting uniformly spaced markings formed by the aligned first and second images.

2. The metrology method according to claim 1, wherein aligning the first image and the second image on the target site includes forming an aligned image of a known size.

3. The metrology method according to claim 1, wherein measuring the dimension of the target site includes counting uniformly spaced circles formed by the aligned first and second images.

4. A metrology method comprising:
   projecting first and second images on an image plane;
   aligning the first image and the second image on a target site different from the image plane by synchronously adjusting a zoom factor for projecting the first image and an angle for projecting the second image; and
   measuring a dimension of the target site by visually comparing the aligned first and second images with the target site.

5. The metrology method according to claim 4, wherein projecting the first and second images includes projecting a light beam through a pattern on a mask.

6. The metrology method according to claim 4, wherein measuring the dimension of the target site includes counting uniformly spaced markings formed by the aligned first and second images.

7. The metrology method according to claim 4, wherein aligning the first image and the second image on the target site includes forming an aligned image of a known size.

8. The metrology method according to claim 4, wherein projecting the first and second images on the image plane includes projecting at least one of the first image and the second image by a point source projector.

9. The metrology method according to claim 4, wherein projecting the first and second images includes splitting a single beam.

10. The metrology method according to claim 4, wherein projecting the first and second images includes projecting the first and second images using two projectors.

* * * * *